United States Patent [19]

Stoffelsma et al.

[11] 4,053,656

[45] Oct. 11, 1977

[54] FOODSTUFFS FLAVORED WITH NEW MERCAPTO ALCOHOLS AND MERCAPTOALKYL ESTERS

[75] Inventors: Jan Stoffelsma, Hoevelaken; Jacob Pypker, Bilthoven, both of Netherlands

[73] Assignees: Polak's Frutal Works B.V.; Douwe Egberts Koninklijke Tabaksfabriek-Koffiebranderijen-Theehandel N.V., both of Amersfoort, Netherlands

[21] Appl. No.: 683,753

[22] Filed: May 6, 1976

Related U.S. Application Data

[62] Division of Ser. No. 347,624, April 4, 1973, Pat. No. 3,970,689.

[51] Int. Cl.² .................. A23L 1/226; A23L 1/234; A23L 1/235
[52] U.S. Cl. .................................................. 426/535
[58] Field of Search ........................................ 426/535

[56] References Cited

U.S. PATENT DOCUMENTS 3,970,689  7/1976  Stoffelsma et al. ............... 260/488 F

*Primary Examiner*—Joseph M. Golian
*Attorney, Agent, or Firm*—William S. Alexander

[57] ABSTRACT

New compounds having the formula

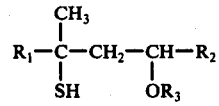

I wherein $R_1$ represents a hydrocarbon moiety having from 1 to 7 carbon atoms, $R_2$ is hydrogen, methyl or ethyl, and $R_3$ is hydrogen, formyl or acetyl. The compounds are useful in the preparation, modification and intensification of a great variety of flavor and perfume compositions.

3 Claims, No Drawings

FOODSTUFFS FLAVORED WITH NEW MERCAPTO ALCOHOLS AND MERCAPTOALKYL ESTERS

This is a divisional of application Serial No. 347,624, filed Apr. 4, 1973 now U.S. Pat. No. 3,970,689.

This invention relates to new mercapto alcohols and esters thereof, more particularly γ-mercapto alcohols and their formates and acetates. These compounds possess interesting olfactive properties and are therefore useful in the prepartion, modification and intensification of a great variety of flavour and perfume compositions.

The compounds of the invention can be represented by the general formula I,

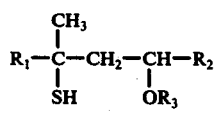

I wherein $R_1$ represents a hydrocarbon moiety having 1 to 7 carbons, $R_2$ represents hydrogen, methyl or ethyl, and $R_3$ represents hydrogen, formyl or acetyl. $R_1$ can be a straight-chain or branched-chain alkyl radical such as a methyl, ethyl, n-propyl, isopropyl, n-butyl, isobutyl, n-pentyl, isopentyl, n-hexyl, n-heptyl, or a branched-chain or straight-chain alkenyl radical such as a hexenyl radical or an isohex-3-en-1-yl radical.

The compounds of the present invention have a very penetrating odour when smelled in high concentrations. In diluted form and under suitably chosen conditions, they develop very pleasant and important odour and flavour notes. For example, depending on dilution and in the present of other organoleptically active compounds, they can develop fruity, green, burnt, roasted or toasted, smoked, and meat- and vegetable-like odour and flavour notes or fortify such notes. The induced notes have a highly natural character. The compounds of this invention can be applied in perfume compositions or in perfumed products such as cleaning agents, cosmetic products, waxes, tooth pastes. They are also useful as flavouring compounds in the preparation of foods or in the preparation of food flavourings, beverages, foods for animals, pharmaceutical products and tobacco products. They can be used as such or together with other flavouring compounds to modify, to improve or to fortify the aroma of foodstuffs such as fruits, vegetables, meats, cereals and other natural aromas. The area of applicability is a very wide one: the use in currant flavourings and in compositions requiring black current bud and buchu type notes, and the use in flavours with roasted type notes could be mentioned as examples. It may be clear that in the present invention the conception "foodstuff" also includes products such as chocolate, coffee and tea. In fact, the compounds of the invention are of special importance for application in coffee and coffee products.

Depending on the odour or flvour type to be created, modified, improved or fortified, and depending on the individual strength, the compounds of this invention produce their desired effects within the very wide range of from $10^{-12}$ to $10^{-2}$ gram per gram finished product.

Although nearly all compounds represented by formula I possess the above-mentioned properties, the preferred compunds of formula I are those in which $R_1 = CH_3$, $R_2 = H$ or $CH_3$, and $R_3 = H$, OCH or $OCCH_3$. In other words, the following compounds:

| | | |
|---|---|---|
| Ia | $CH_3-\underset{\underset{SH}{|}}{\overset{\overset{CH_3}{|}}{C}}-CH_2-CH_2OH$ | 3-mercapto-3-methylbutanol |
| Ib | $CH_3-\underset{\underset{SH}{|}}{\overset{\overset{CH_3}{|}}{C}}-CH_2-CH_2OOCH$ | 3-mercapto-3-methylbutyl formate |
| Ic | $CH_3-\underset{\underset{SH}{|}}{\overset{\overset{CH_3}{|}}{C}}-CH_2-CH_2OOCCH_3$ | 3-mercapto-3-methylbutyl acetate |
| Id | $CH_3-\underset{\underset{SH}{|}}{\overset{\overset{CH_3}{|}}{C}}-CH_2-\underset{\underset{OH}{|}}{CH}-CH_3$ | 4-mercapto-4-methylpentan-2-ol |
| Ie | $CH_3-\underset{\underset{SH}{|}}{\overset{\overset{CH_3}{|}}{C}}-CH_2-\underset{\underset{OOCH}{|}}{CH}-CH_3$ | 4-mercapto-4-methylpent-2-yl formate |
| If | $CH_3-\underset{\underset{SH}{|}}{\overset{\overset{CH_3}{|}}{C}}-CH_2-\underset{\underset{OOCCH_3}{|}}{CH}-CH_3$ | 4-mercapto-4-methylpent-2-yl acetate |

Compounds I a–f can be described organoleptically as mild greenish, oniony, sulfury, sweaty. Wide differences in threshold value ae observed (from 0.01 down to 0.000001 p.p.m.; tasted/smelled in aqueous solution at 70° C).

The new mercapto alcohols and their esters represented by formula I can be prepared from the mono-olefinic aldehydes and ketones represented by formula II. The addition of thioacetic acid produces the β-acetylthio carbonyl compounds III.

I

-continued

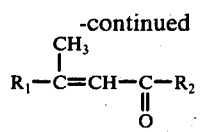

III

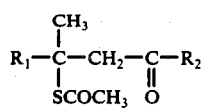

The addition of thioacetic acid can be performed with or without using a catalyst and at moderate temperatures. The β-acetylthioaldehydes and β-acetylthioketones are added to a solution of sodium borohydride, thus producing compounds with formula I in which $R_3$ represents acetyl. A treatment of these acetates with an excess of a low boiling alcohol containing a catalytic amount of dry hydrogen chloride produces the alcohols with formula I, in which $R_3$ represents hydrogen. The alcohols thus obtained can be esterified with formyl acetate or with a reaction mixture of formic acid and acetic anhydride to their formates with formula I, in which $R_3$ represents formyl. Formyl acetate and reaction mixtures of formic acid and acetic anhydride are easily prepared according to W. Stevens and A. van Es, Rec. Trav. Chim. 83, 863, 1287 (1964).

EXAMPLE I

Preparation of 3-mercapto-3-methylbutyl acetate a. Preparation of 3-acetylthio-3-methylbutanal
Thioacetic acid (35 g) was slowly added with stirring to 38 g of 3-methylbut-2-enal. The reaction was run in a nitrogen atmosphere, the temperature kept between 26° C and 32° C.
After standing overnight the reaction mixture was distilled in vacuum, yielding 63 g (87%) of 3-acetylthio-3-methylbutnal b.p. 54°–55°C/1 mmHg, $n_D^{20}$ 1.4810.

b. Preparation of 3-mercapto-3-methylbutyl acetate
3-Acetylthio-3-methylbutanal (32 g) was dissolved in 50 ml of methanol. A solution of 3.5 g of $NaBH_4$ and 0.3 g of $NaOCH_3$ in 50 ml of methanol was added dropwise through a dropping funnel and with stirring keeping the temperature of the reaction mixture between 20° C and 25° C with ice water. After the solution of $NaBH_4$ had been added the mixture was stirred for one hour, then the same volume of water was added with stirring and mixture was extracted twice with n-pentane. The pentane extract was washed with an aqueous solution of sodium chloride and dried over sodium sulphate. After concentrating the dried solution, the residue was distilled yielding 25 g (77%) of 3-mercapto-3-methylbutyl acetate, b.p. 39°–40° C/1 mm, $n_D^{20}$ 1.4616.

EXAMPLE II

Preparation of 3-mercapto-3-methylbutanol

3-Mercapto-3-methylbutyl acetate (38 g) was dissolved in 200 ml of methylalcohol containing 1% of dry hydrogen chloride. After standing overnight the solution was neutralized with solid sodium carbonate. Methanol and methyl-acetate were distilled off at 12 mmHg (room temperature). The residue was dissolved in diethyl ether, washed neutral, dried over sodium sulphate and concentrated. Distillation of the residue yielded 26 g (93%) of 3-mercapto-3-methylbutanol, b.p. 45°–46° C/1.5 mm, $n_D^{20}$ 1.4792.

EXAMPLE III

Preparation of 3-mercapto-3-methylbutyl formate

A mixture of 21.5 g of acetic anhydride and 10.8 g of formic acid was heated at 45° C for 1½ hours. After cooling 1.7 g of pyridine was added and, with stirring, 19.5 g of 3-mercapto-3-methylbutyl alcohol in the course of 5 minutes. The temperature of the reaction mixture slowly rose to 45° C. After completion of the addition, the reaction mixture was held at 45° C for 4 hours and then cooled to room temperature. It was dissolved in ether, washed five times with 3% aqueous $NaHCO_3$ solution and finally with NaCl solution to neutral.
The ethereal solution was dried over sodium sulphate, filtered and concentrated. Distillation of the residue yielded 21.5 g (90%) of 3-mercapto-3-methylbutyl formate b.p. 30°–31° C/1 mm, $n_D^{20}$ 1.4610.

EXAMPLE IV

Preparation of 4-mercapto-4-methylpent-2-yl acetate

4-Acetylthio-4-methylpentan-2-one (17 g, prepared as described by R. Brown, W.E. Jones and A.R. Pinder, J. Chem. Soc. 1951, 2123), was dissolved in 25 ml of methanol. A solution of 1.945 g of $NaBH_4$ and of 0.1 g of $NaOCH_3$ in 25 ml of methanol was added dropwise through a dropping funnel, keeping the temperature of the reaction mixture between 10° and 25° C by occasionally cooling with ice water. After standing overnight the reaction mixture was diluted with a same volume of water and extracted twice with n-pentene. The pentane extract was washed neutral with an aqueous solution of sodium chloride, dried over sodium sulphate and concentrated. Distillation of the residue yielded 19 g (52.5%) of 4-mercapto-4-methylpent-2-yl acetate, b.p. 37°–39° C/1 mm, $n_D^{20}$ 1.4530.

EXAMPLE V

Preparation of 4-mercapto-4-methylpentan-2-ol

4-Mercapto-4-methylpent-2-yl acetate (32 g) was dissolved in 200 ml of methanol containing 1% of dry hydrogen chloride. After standing overnight the reaction mixture was neutralized with solid sodium carbonate. The solvent and methyl acetate were distilled off at 12 mmHg at room temperature. The residue was dissolved in diethyl ether, washed neutral, dried over sodium sulphate and concentrated. Distillation of the residu yielded 14 g (57.6%) of 4-mercapto-4-methylpentan-2-cl, b.p. 32°C/1 mm, $n_D^{20}$ 1.4724.

EXAMPLE VI

Preparation of 4-mercapto-4-methylpent-2-yl formate

A mixture of 12.3 g of acetic anhydride and 6.2 g of formic acid was heated at 40° C for 1 hour. After cooling to 20° C 1 g of pyridine was added and subsequently, with stirring, 15 g of 4-mercapto-4-methylpentan-2-ol in the course of 10 minutes. The temperature of the reaction mixture slowly rose to 28° C. After standing overnight it was dissolved in diethylether, washed five times with 3% aqueous $NaHCO_3$ solution and then with aqueous NaCl solution to neutral. The ethereal solution was dried over $Na_2SO_4$ and concentrated. Distillation of the residue yielded 10.5 g (58%) of 4-mercapto-4-methylpent-2-yl formate, b.p. 30°–32° C/1 mm, $n_D^{20}$ 1.4564.

EXAMPLE VII

Preparation of 3-mercapto-3-methyloct-1-yl acetate a. Preparation of 3-acetylthio-3-methyloctanal Freshly distilled thioacetic acid (64 g) was added with stirring and occasional cooling to a mixture of 98 g 3-methyloct-2-enal and 25 mg of benzoyl peroxide. After 5 hours of reflux the mixture was distilled in vacuo through a 20 cm vigreux column yielding 62.5 g (41.3%) of 3-acetylthio-3-methyloctanal, b.p. 100°–112° C/0.5 mm.

b. Preparation of 3-mercapto-3-methyloct-1-yl acetate

A solution of 6 g sodium borohydride and 1 g of sodium methylate in 150 ml of methanol was added with stirring to a solution of 65 g of the acetylthioaldehyde in 150 ml methanol while keeping the temperature between 20° and 25° C by efficient cooling. After stirring for an additional 3 hours at room temperature the reaction mixture was heated at 60° C for 30 minutes. Then methanol was removed in vacuo and the residue was washed with 100 ml of water.

The separated aqueous layer was then extracted twice with 100 ml of ether. The combined organic layers were washed with water and then dried over sodium sulfate. After filtration and evaporation of the solvent, the residue was distilled in vacuo through a 20 cm vigreux column yielding 20 g (30.4%) of 3-mercapto-3-methyloct-1-yl acetate, b.p. 92°–94° C/0.3 mm; $n_D^{20}$ 1.4634.

EXAMPLE A

Example of a composition in parts by weight:

500 — black currant concentrated extract
495 — black current bud extract
1 — lie de vin
0.01 cassia oil
0.02 — oil of petitgrain
5 — vanilla extract
0. 01—3-mercapto-3-methylbutanol
Concentration: 0.1% per liter tasting beverage.

We claim:

1. A foodstuff which has added thereto about $10^{-12}$ to $10^{-2}$ gram per gram of a compound having the formula

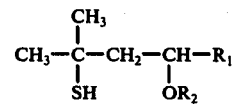

where $R_1$ is hydrogen or methyl and $R_2$ is hydrogen, formul, or acetyl, to develop or fortify a fruity, green, burnt, roasted, or smoked flavor note.

2. The foodstuff of claim 1 wherein the compound is 3-mercapto-3-methyl butyl acetate and the foodstuff is a coffee flavored beverage.

3. The foodstuff of claim 1 wherein the compound is 3-mercapto-3-methyl butanol and the foodstuff is a black currant extract.

* * * * *

UNITED STATES PATENT OFFICE
CERTIFICATE OF CORRECTION

Patent No. 4,053,656　　　　　　　　　　Dated October 11, 1977

Inventor(s) Stoffelsma & Pijpker

It is certified that error appears in the above-identified patent and that said Letters Patent are hereby corrected as shown below:

Column 1, line 12;

"prepartion" should be --preparation--.

Column 2, line 17;

"flvour" should be --flavour--.

UNITED STATES PATENT OFFICE
CERTIFICATE OF CORRECTION

Patent No. 4,053,656      Dated October 11, 1977

Inventor(s) Stoffelsma & Pijpker

It is certified that error appears in the above-identified patent and that said Letters Patent are hereby corrected as shown below:

Column 6, Example B was omitted - should read as follows:

Example B

Another example of a composition in parts by weight:

500    concentrated coffee extract 300    fresh aqueous coffee extract 200    coffee distillate 0.01 3-mercapto-3-methylbutyl acetate Concentration: 0.1% per liter tasting beverage.

Signed and Sealed this

Seventh Day of March 1978

[SEAL]

Attest:

RUTH C. MASON
Attesting Officer

LUTRELLE F. PARKER
Acting Commissioner of Patents and Trademarks